(12) United States Patent
Carney et al.

(10) Patent No.: US 6,403,627 B1
(45) Date of Patent: *Jun. 11, 2002

(54) SPIN TRAPPING PHARMACEUTICAL COMPOSITIONS AND METHODS FOR USE THEREOF

(75) Inventors: John M. Carney, Lexington, KY (US); Robert A. Floyd, Oklahoma City, OK (US)

(73) Assignees: Oklahoma Medical Research Foundation, Oklahoma City, OK (US); University of Kentucky Foundation, Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/357,297

(22) Filed: Jul. 20, 1999

Related U.S. Application Data

(63) Continuation of application No. 08/969,344, filed on Nov. 28, 1997, now Pat. No. 6,002,001, which is a continuation of application No. 08/167,900, filed on Jul. 29, 1994, now abandoned, which is a continuation-in-part of application No. 08/212,800, filed on Mar. 15, 1994, now Pat. No. 5,622,994, which is a continuation of application No. 08/052,870, filed on Apr. 23, 1993, now abandoned, which is a continuation of application No. 07/716,952, filed on Jun. 18, 1991, now abandoned.

(51) Int. Cl.$^7$ ............................................. A61K 31/415
(52) U.S. Cl. ........................ 514/400; 514/576; 514/658
(58) Field of Search ................. 514/400, 576, 514/658

(56) References Cited

U.S. PATENT DOCUMENTS

| | | | |
|---|---|---|---|
| 3,296,145 A | 1/1967 | Findlan et al. ............... 252/106 |
| 3,767,818 A | 10/1973 | Dorschner et al. .......... 424/330 |
| 3,775,122 A | 11/1973 | Schlesinger ..................... 96/28 |
| 3,834,073 A | 9/1974 | Dorschner et al. ........... 47/57.6 |
| 3,849,934 A | 11/1974 | Dorschner et al. ........... 47/57.6 |
| 4,153,722 A | 5/1979 | Campbell et al. ............ 424/304 |
| 4,197,314 A | 4/1980 | Campbell et al. ............ 424/311 |
| 4,214,003 A | 7/1980 | Campbell et al. ............ 424/301 |
| 4,216,231 A | 8/1980 | Tanida et al. ................ 424/330 |
| 4,224,340 A | 9/1980 | Campbell et al. ............ 424/304 |
| 5,025,032 A | * 6/1991 | Carney et al. ............... 514/400 |
| 5,036,097 A | 7/1991 | Carney et al. ............... 514/400 |
| 5,157,031 A | * 10/1992 | Schwartz et al. ............ 514/177 |
| 5,340,568 A | * 8/1994 | Piazza et al. .................. 424/59 |
| 5,405,874 A | 4/1995 | Carney et al. ............... 514/619 |
| 5,475,032 A | * 12/1995 | Carney et al. ............... 514/576 |
| 5,578,617 A | 11/1996 | Carney et al. ............... 514/395 |
| 5,622,994 A | 4/1997 | Carney et al. ............... 514/643 |
| 5,681,965 A | 10/1997 | Carney et al. ............... 548/542 |

FOREIGN PATENT DOCUMENTS

GB      1109473      4/1968

OTHER PUBLICATIONS

Lehninger et al., Principles of Biochemistry pp. 341, 344 and 886, copyright 1993.*

\* cited by examiner

*Primary Examiner*—Dwayne C. Jones
(74) *Attorney, Agent, or Firm*—Birch, Stewart, Kolasch & Birch, LLP

(57) ABSTRACT

Spin trapping compositions in general have now been discovered to be effective in treating a variety of disorders, including disorders such as those arising from ischemia, infection, inflammation, exposure to radiation or cytotoxic compounds, not just of the central and peripheral nervous systems but of peripheral organ disease having a wide variety of etiologies. In the preferred embodiment, the compositions for treating tissue damage from ischemia contain PBN, or active derivatives thereof, in a suitable pharmaceutical carrier for intravenous, oral, topical, or nasal/pulmonary administration. Other preferred spin-trapping agents include 5,5-dimethyl pyrroline N-oxide (DMPO), α-(4-pyridyl-1-oxide)-N-tert-butylnitrone (POBN), and (TEMPO) and spin-trapping derivatives thereof. Examples of derivatives of PBN include halogenated derivatives, bifunctional derivatives, conjugates with drugs or targeting molecules, dimers and cyclodextran polymers of PBN. Many different disorders can be treated using these compounds, including diseases or disorders of the central and peripheral nervous systems, and disorders arising from ischemia, infection, inflammation, oxidation from exposure to radiation or cytotoxic compounds, as well as due to naturally occurring processes such as aging.

20 Claims, No Drawings

SPIN TRAPPING PHARMACEUTICAL COMPOSITIONS AND METHODS FOR USE THEREOF

This application is a continuation of Ser. No. 08/969,344, filed on Nov. 28,1997 now U.S. Pat. No. 6,002,001, which is a continuation of Ser. No. 08/167,900, filed Jul. 29, 1994, abandoned on Dec. 2, 1997, which is a continuation-in-part of Ser. No. 08/212,800, filed Mar. 15, 1994, now U.S. Pat. No. 5,622,994, which is a continuation of Ser. No. 08/052,870, filed Apr. 23, 1993, abandoned on Mar. 22, 1994, which is a continuation of Ser. No. 07/716,952, filed Jun. 18, 1991, abandoned on Apr. 26, 1993.

BACKGROUND OF THE INVENTION

The present invention is a method and compositions containing spin trapping agents for the treatment of dysfunctions and disease conditions arising from oxidative damage.

Oxygenated tissue suffers damage, in many cases permanent damage, if it becomes ischemic and is then reperfused. Brain appears to be highly susceptible to ischemia/reperfusion injury. Certain areas of the brain, for example, the hippocampus and spinal cord, are more susceptible than other regions of the brain. As a result, ischemia/reperfusion injury to brain may have a multiplicative effect simply because of the necessity for complete integrity of all regions in order to have proper functioning.

Free radicals have been postulated to be mediators of reperfusion damage. The most likely sites for production of such radicals as the superoxide ($O^{-2}$) and hydroxyl (OH—) species, and the precursor oxygen species, $H_2O_2$ are the mitochondrial respiratory chain specific enzymes and the sequences catalyzed by cyclooxygenase and lipoxygenase. However, radicals are also formed during autoxidation of many compounds (e.g., catecholamines). Ischemia appears to favor a spurt of free-radical formation, resulting in oxidation of polyenoic free fatty acids, release and reuptake of catecholamines, and oxidation of hypoxanthine by xanthine oxidase. Despite these events occurring during recirculation, when the $O_2$ supply is restored, they represent metabolic cascades triggered by agonist-receptor interactions, energy failure, and/or calcium influx during the insult.

Although free radical formation has been postulated to be a likely cause of ischemic damage, it was difficult to directly demonstrate that such formation occurs and/or that it was sufficiently pronounced to overwhelm the antioxidative defense of the tissue, as reviewed by Curran, et al., *Mol. Cell. Biol.* 5, 167–172 (1985). Phenyl butyl nitrone (PBN) has been used in a number of these in vitro research studies using spin trapping to look for free radicals, but until demonstrated by the data in U.S. Ser. No. 07/422,651, now U.S. Pat. No. 5,025,032, there has been no data to support the proposition that it could be useful in vivo, particularly with respect to treatment of tissue damage in the central nervous system. In vivo, the drug must be able to both cross the blood brain barrier and act in a manner which reduces tissue damage during or following ischemia.

In U.S. Ser. No. 07/589,177, abandoned on Mar. 5, 1993, the use of PBN and related compounds, as well as 5,5-dimethyl pyrroline N-oxide (DMPO) and α-(4-pyridinyl-1-oxide)-N-tert-butylnitrone (POBN), for treatment of aging was described. Age related changes in central nervous system function have generally been associated with the loss of cells, a widening of lateral ventricles and deficits in short term memory. The precise mechanisms of functional changes as a result of aging, or other diseases associated with aging, have not generally been agreed upon, including several mechanisms for the generation of oxidized material in the brain. A marked reduction in certain neurotransmitter receptor systems has been associated with increased oxidation of proteins. For example, decreases in muscarinic receptors and other cholinergic systems have been characterized as they relate to alterations in functions in Alzheimers disease. It is now known that the processes of aging and Alzheimer's disease are associated with oxidation of brain proteins. It has also been hypothesized that aging is associated with multiple minor periods of ischemia (multi-infarct conditions or transient ischemia attacks) which, over a period of time, may give rise to the production of oxidized protein.

The demonstration in a variety of systems, both neural and nonneural, that there is an age related enhancement of the level of oxidized protein in tissue gives rise to the possibility that age related dysfunctions in the central nervous system may be associated with the build-up of oxidized proteins and oxidized macromolecules within neurons throughout the central nervous system. The hypothesis is that cells which have a buildup of oxidized protein are less functional and less able to maintain the specified role of those cells in that particular area of the central nervous system. The data presented in U.S. Ser. No. 07/589,177 abandoned on Mar. 5, 1993, was the first report of substantial investigations in which alterations in the oxidized protein burden of the central nervous system was manipulated and correlated with a functional outcome on the part of the animal. There are a number of other disorders and diseases which have now been postulated to be associated with oxidation of proteins, including many central nervous system (CNS) diseases besides stroke and aging, including Parkinsonism, trauma, vascular headaches, cerebral palsy, diabetic neuropathy,and neuroanesthesia adjunct, as well as peripheral nervous system diseases such as diabetic peripheral neuropathy and traumatic nerve damage, as well as peripheral organ diseases. Examples of peripheral organ diseases include atherosclerosis, pulmonary fibrosis, pancreatitis, angioplasty, multiple organ failure, burns, decubitus ulcers, and ischemic bowel disease.

It is therefore an object of the present invention to provide spin-trapping compositions and methods for use thereof which are useful in preventing or reversing ischemic damage in vivo, in the CNS, resulting from diseases such as stroke, aging, Parkinsonism, concussion, Berry aneurysm, ventricular hemorrhage and associated vasospasm, spinal cord trauma, vascular headaches, and neuroanesthesia adjunct.

It is another object of the present invention to provide spin-trapping compositions, and methods for use thereof, which are useful in treating damage in vivo resulting from peripheral nervous system diseases, including diabetic peripheral neuropathy and traumatic nerve damage.

It is still another object of the present invention to provide spin-trapping compositions, and methods for use thereof, which are useful in preventing or reversing free radical damage in vivo resulting from injury, infection and inflammation, especially peripheral organ diseases such as chronic obstructive pulmonary disease (COPD), atherosclerosis (both diabetic and spontaneous), pulmonary fibrosis due to anti-cancer treatment, drug treatment, pancreatitis, angioplasty, multi-organ failure following trauma, burns (chemical, thermal, and radiation), the progressive loss of myocardial cells leading to cardiac failure as a result of age-related oxidation, and ischemic bowel disease.

It is another object of the present invention to provide spin-trapping compositions for use in the process of organ transplantation and preservation.

It is a further object of the present invention to treat disorders not associated with oxidation, such as undesirable HDL/LDL ratios, as well as the treatment of damage arising from exposure to cytotoxic compounds and radiation.

SUMMARY OF THE INVENTION

Spin trapping compounds in general have now been discovered to be effective in treating a variety of disorders, including disorders such as those arising from ischemia, infection, inflammation, exposure to radiation or cytotoxic compounds, not just of the central and peripheral nervous systems but of peripheral organ disease having a wide variety of etiologies.

Spin trapping compounds as referred to herein are molecules that (1) have an unpaired electron; (2) form a stable compound or complex with a free radical; and (3) are nontoxic, i.e., have a therapeutic index (margin of safety; $EC_{50}/LC_{50}$) of 3 or more.

The spin traps provide a unique signal that can be measured by electron spin spectroscopy (ESR) when it binds to a free radical. For example, the oxidation of brain tissue involves a free radical intermediate. Brain tissue that has been treated with PBN has been monitored by ESR. As a free radical on a lipid or protein is generated, PBN traps the radical and forms a covalently bound product with the material, which has a characteristically unique ESR signal. The PBN-(lipid or protein) has then been isolated and identified.

A wide range of spin trapping compounds are disclosed in detail herein. Other spin traps that meet the above three requirements are known to those of skill in the art of organic and medicinal chemistry. An essential criteria for the selection of the spin trap is that it actively trap free radicals without cytotoxicity, and that in the applications where access to the CNS is required for efficacy, that the compounds pass through the blood brain barrier.

Many different disorders can be treated using these compounds, including diseases or disorders of the central and peripheral nervous systems, and disorders arising from ischemia, infection, inflammation, oxidation from exposure to radiation or cytotoxic compounds, as well as due to naturally occurring processes such as aging.

DETAILED DESCRIPTION OF THE INVENTION

The term alkyl, as used herein, unless otherwise specified, refers to a saturated straight, branched, or cyclic hydrocarbon of $C_1$ to $C_{10}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl, and cyclohexyl.

The term alkenyl, as referred to herein, and unless otherwise specified, refers to a straight, branched, or cyclic (in the case of $C_{5-6}$) hydrocarbon of $C_2$ to $C_{10}$ with at least one double bond.

The term aryl, as used herein, and unless otherwise specified, refers to phenyl or substituted phenyl, wherein the substituent is halo or lower alkyl.

The term halo, as used herein, includes fluoro, chloro, bromo, and iodo.

The term aralkyl refers to an aryl group with an alkyl substituent.

The term alkaryl refers to an alkyl group that has an aryl substituent.

The term halo (alkyl or alkenyl) refers to an alkyl or alkenyl group in which at least one of the hydrogens in the group has been replaced with a halogen atom. The term haloalkyl specifically includes trifluoromethyl.

The term aralkyl refers to an aryl group with an alkyl substituent.

The term pharmaceutically active derivative refers to any compound that upon administration to the recipient, is capable of providing directly or indirectly, the compounds disclosed herein.

The term alkaryl refers to an alkyl group that has an aryl substituent.

The term nontoxic refers to a compound that has a therapeutic index of at least three.

The invention disclosed herein includes pharmaceutical compositions that contain spin trapping compounds or pharmaceutically acceptable derivatives or salts thereof for use in medical therapy, for example for the treatment or prophylaxis of disorders such as those arising from ischemia, infection, inflammation, exposure to radiation or cytotoxic compounds, not just of the central and peripheral nervous systems but of peripheral organ disease having a wide variety of etiologies.

The invention also includes the use of spin trapping agents and pharmaceutically acceptable derivatives or salts thereof in the manufacture of a medicament for treatment or prophylaxis of disorders such as those arising from ischemia, infection, inflammation, exposure to radiation or cytotoxic compounds, not just of the central and peripheral nervous systems but of peripheral organ disease having a wide variety of etiologies.

It has now been discovered that spin-trapping agents are generally useful in preventing or treating symptoms associated with a very wide range of disorders of the central and peripheral nervous system, as well as peripheral organ disfunction and disease, including not just aging, trauma, ischemia but disorders as disparate as undesirable ratios of lipoproteins, ulcerative colitis, and damage arising from exposure to radiation and cytotoxic compounds (chemotherapeutic compounds, in most instances).

Useful Spin-trapping Compounds.

PBN and derivatives thereof.

The preferred spin-trapping compounds are phenyl N-tert-butylnitrone, also referred to as α-phenyl t-butyl nitrone (PBN), and derivatives thereof of the formula:

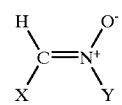

wherein:

X is phenyl, imidazolyl, phenothiazinyl or

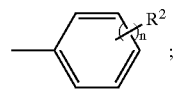

n=1–5, preferably 1–3;

$R^2$=independently (can vary within the molecule) halogen, alkyl, oxyalkyl, alkenyl, oxyalkenyl, OH, $NH_2$, NHZ, $NZ_2$, NO,

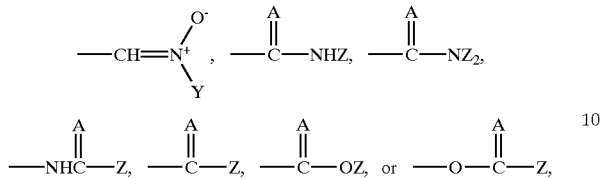

—$SO_3H$, —$OSO_3H$, SH, —S(alkyl), —S(alkenyl), and haloalkyl, specifically including —$CF_3$;

A=O or S; and

Z is a $C_1$ to $C_6$ straight, branched, alkyl or cyclic group; and

Y is a tert-butyl group that can be hydroxylated or acetylated at one or more positions; phenyl or

PBN is the most preferred compound at this time, having no measurable effect on normal or uninjured cells, although a number of derivatives are also useful, including hydroxy derivatives, especially 2-, 3- or 4-hydroxyphenyl t-butyl nitrone and phenyl (mono-, di- or trihydroxy) tert-butyl nitrone; PBN esters, especially esters which release 2-, 3-, or 4-hydroxyphenyl t-butyl nitrone such as the acetoxy derivative; 2-, 3-, or 4-carboxyphenyl t-butyl nitrone; phenyl hydroxybutyl nitrone; alkoxyl derivatives, especially alkoxyl derivatives which release 2-, 3-, or 4-hydroxyphenyl t-butyl nitrone, for example, the 2-, 3-, or 4- methoxyphenyl derivatives of PBN; and acetamide derivatives, especially acetamide derivatives which release 2-, 3-, or 4- aminophenyl t-butyl nitrone; diphenyl nitrone (PPN) and the analogous diphenyl nitrone derivatives; N-tert-butyl-α-(4-nitrophenyl) nitrone; and N-tert-butyl-α-(2-sulfophenyl) nitrone. As used herein, "PBN" refers to both phenyl N-tert-butyl nitrone and derivatives thereof, unless otherwise stated. Formulas for PBN and specific derivatives thereof are:

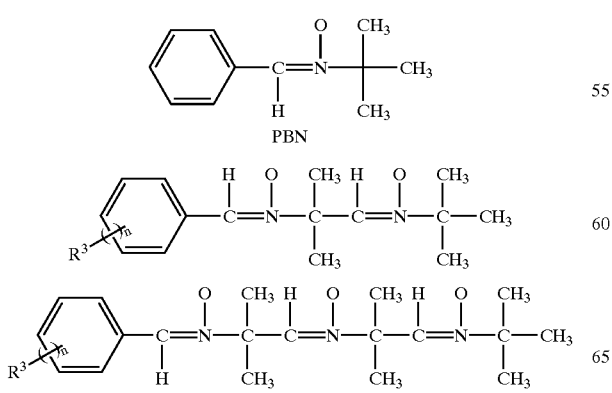

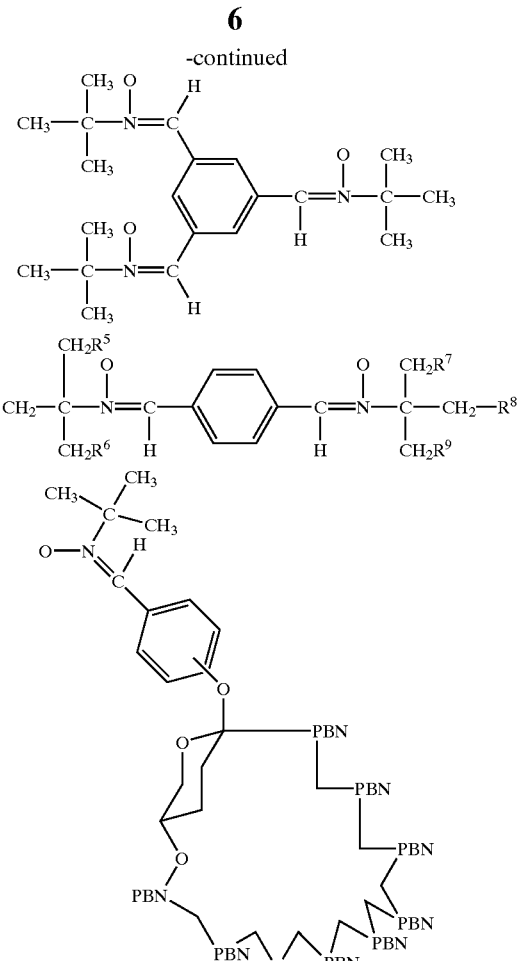

Example of PBN (α, β, or γ) CYCLODEXTRAN POLYMER wherein PBN =

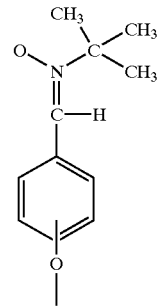

connected through one or more hydroxyl moieties of the cyclodextran

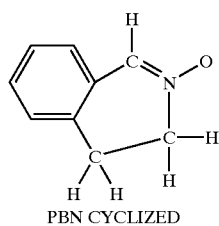

PBN CYCLIZED

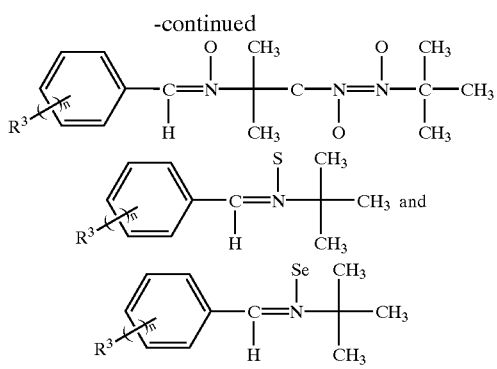

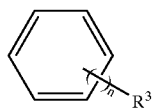

wherein R³=independently R² (that can vary within the molecule) or H;

and R⁴ to R⁹ are independently R², H or

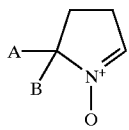

Other spin-trapping agents can also be used, such as 5,5-dimethyl pyrroline N-oxide (DMPO), α-(4-pyridyl 1-oxide)-N-tert-butylnitrone (POBN), 3,3,5,5-tetramethyl-1-pyrroline N-oxide, and 2,4,4,6-tri-tert-butylnitrosobenzene (BNB), and spin-trapping derivatives thereof. Many compounds are commercially available or can be synthesized using methods known to those skilled in the art. α-phenyl-N-phenylnitrone compounds for use as topical antiinflammatories are described by U.S. Pat. No. 4,224,340 to Campbell, et al., the teachings of which are incorporated herein.

DMPO and Derivatives Thereof

The general formula for DMPO, and specific derivatives are:

wherein A and B are independently —R², —CH₂OH, —CH₂OW, or

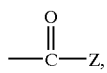

n is an integer from 1 to 5; and

W is

specifically including

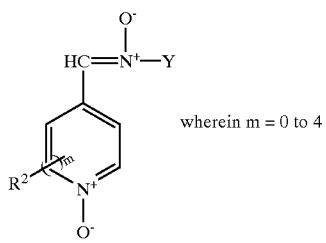

or —Z

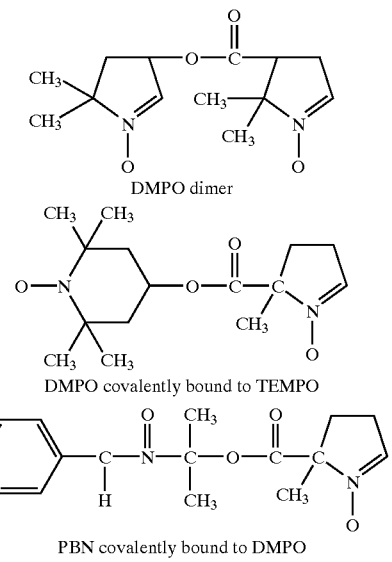

POBN and Derivatives Thereof.

The general formula for POBN is:

$$HC=N^+—Y$$

wherein m = 0 to 4

TEMPO and Derivatives Thereof.

2,2,6,6-Tetramethyl piperidinooxy (TEMPO) is a nitroxide organic free radical trap. The synthesis and chemistry of nitroxide free radicals is referenced by Galfnley, B. J., pp. 184–238 in *Spin Labeling in Pharmacology* Berliner, L. H., (Academic Press, NY, N.Y. 1976), the teachings of which are incorporated herein. TEMPO and several derivatives thereof can be purchased from Aldrich Chemical Co., as can many other spin traps such as PBN, DMPO, and POBN and some of their derivatives.

As discussed above, the important criteria for these compounds is that they must trap free radicals, especially hydroxy and superoxide radicals, while remaining non-toxic to normal cells. In those applications where the compound must reach the brain and other parts of the CNS, the compound must also be low molecular weight to pass through the blood brain barrier. In some applications, the higher molecular weight dimers and polymers of the spin trap may have advantages.

Conjugates and Polymers of Spin Trapping Compounds.

In another embodiment, spin trapping compounds are covalently attached to known pharmaceutical agents, by methods known to those skilled in the art. Examples of useful compounds include spin traps covalently bound to antiinflammatories, neuroactive compounds, antioxidants, or calcium channel blockers. Examples as illustrated include conjugates of acetaminophen, dopamine (or DOPA), vitamin E, and nifediphene.

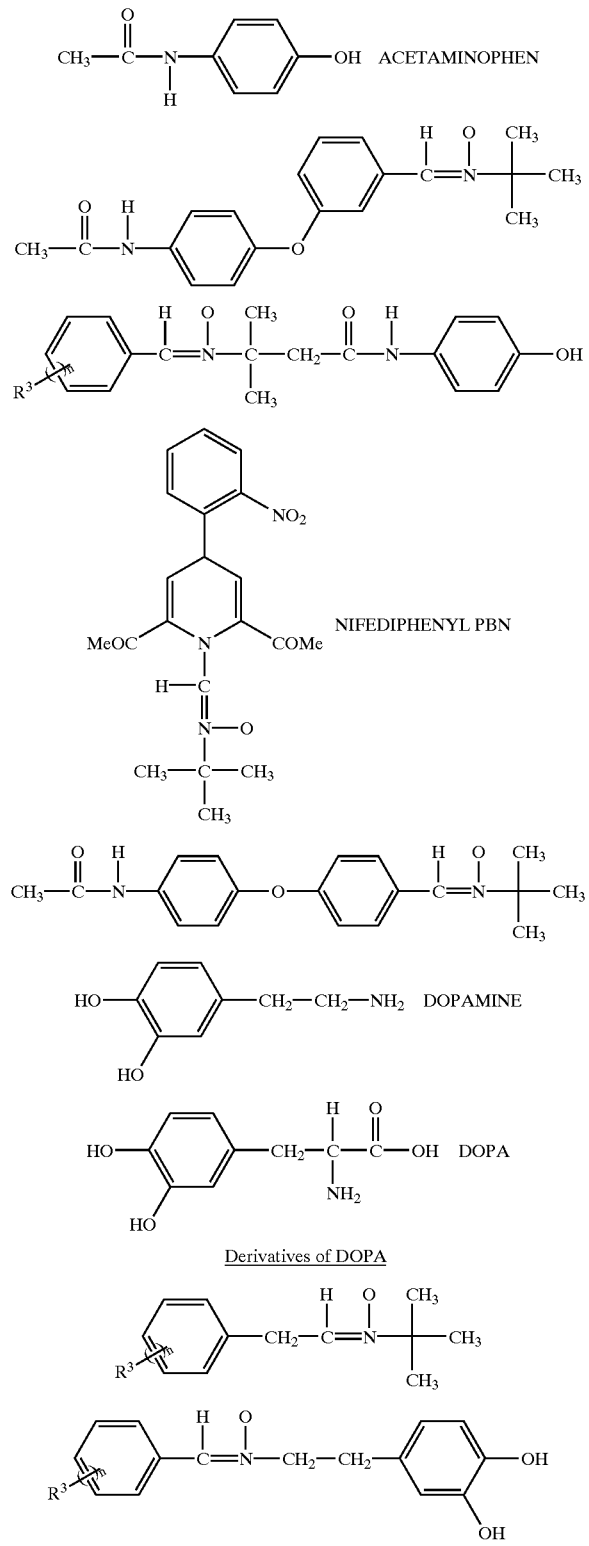

Other drugs that can be covalently bound to the spin traps include calcium channel blockers such as nimodipine, nicardipine, nifedipine, nitrendipine, diltriazam and flunarazine; cardiac glycosides such as digitalis and analogues thereof; adenergic antagonists such as propranalol; metal chelators such as desferal; modified steroids such as lazaroids; antiinflammatories such as prednisone; nonsteroidal antiinflammatories such as acetaminophen, ibuprofen, and indomethacin; antioxidants such as vitamin E; and neuroactive compounds such as L-DOPA. The optimal position to bind the spin trap to the pharmaceutical agent is easily determined using known information on structure activity relationships and bulk tolerance of the pharmaceutical agent. In some cases spacers will be required between the spin-trap and the conjugated compound in order to preserve maximum activity.

Spin traps can also be attached to antibodies or ligands for specific receptors (such as certain hormones, enzymes, or even specific sugars or carbohydrates) which are used to "target" or otherwise concentrate the spin trapping compound. Depending on the structure of the spin trap, as well as the biologically active compound, it may be necessary to insert a spacer between the spin trap and the biologically active compound.

Indications that the compositions are useful in treating.

The spin trap or free-radical scavenger compositions are useful in treating a variety of dysfunctions or disorders characterized by oxidized proteins or lipids in the tissues, cells, or associated fluids (such as the blood). Oxidation of cytosolic protein has been demonstrated to occur in a wide variety of pathological conditions.

Accordingly, compounds which have as their fundamental mechanism of action the interference of production of oxidized protein are useful in the treatment of a wide variety of diseases having what appears at first glance to be widely dissimilar etiologies, because the fundamental cause of the condition is oxidation of protein, nucleic acids, or lipids.

Disorders are generally divided into disorders of the central and peripheral nervous'system and disorders of the peripheral organs.

Disorders of the CNS include stroke, aging, Parkinsonism, concussion, aneurysm, ventricular hemorrhage and associated vasospasm, migraine and other vascular headaches, spinal cord trauma, diabetic retinopathy, and neuroanesthesia adjunct. Disorders of the peripheral nervous system include diabetic peripheral neuropathy and traumatic nerve damage.

Peripheral organ disease includes atherosclerosis (both diabetic and spontaneous), chronic obstructive pulmonary disease (COPD), pancreatitis, pulmonary fibrosis due to chemotherapeutic agents, angioplasty, trauma, burns, ischemic bowel disease, wounds, ulcers and bed sores, lupus, ulcerative colitis, organ transplantation, renal hypertension, overexertion of skeletal muscle, and epistaxis (pulmonary bleeding).

Other conditions associated with excessive oxidation of proteins or lipids that can be treated include undesirable or altered oxidation of low density lipoprotein, and dysfunction from exposure to radiation, including x-ray, ultraviolet, gamma and beta radiation, and cytotoxic compounds, including those used for chemotherapy for cancer and viral infections.

Treatment of Central Nervous System Diseases

Stroke

Multiple in vitro studies, as well as the in vivo data presented in U.S. Ser. No. 07/589,177 abandoned on Mar. 5, 1993, and U.S. Ser. No. 07/422,651 now U.S. Pat. No. 5,025,023, have demonstrated that there are a series of biochemical changes that result in the production of free radicals following ischemia. PBN and other spin-trapping compounds can covalently bind to these radicals and prevent the peroxidation of cellular proteins and fatty acids. The consequence of the trapping of these carbon-centered and oxygen-centered radicals is the termination of the propagation phase of free radical production within the neuron. This interruption of free radical production can decrease the mortality and morbidity seen in strokes.

Aging

Aging has been demonstrated to be associated with the production of abnormally high levels of oxidized proteins. The consequence of this increased level of protein oxidation is an abnormally low level of critical enzymes in the affected cells. While not all cells have been evaluated, it appears from the in vivo data presented in U.S. Ser. No. 07/589, 177abandoned on Mar. 5, 1993, and U.S. Ser. No. 07/422, 651, now U.S. Pat. No. 5,025,032, and reports of in vitro studies, that most, if not all, cells in the body will undergo abnormally high levels of protein oxidation. Decreases in antioxidant systems and abnormally low levels of mitochondrial function have been described. The protein oxidation is thought to arise from oxygen free radicals, largely generated via a metal catalyzed reaction within the cell. Studies have now been conducted that daily administration of a free radical spin trapping compound, PBN, for fourteen days completely reverses this process. Not only is the level of protein oxidation decreased, but the abnormally low level of enzyme activity is restored to normal.

Parkinsonism

Research has indicated that one of the principle sources of dopaminergic damage to the striatum is via free radical mediated oxidation. Dopamine can be oxidized to the neurotoxin 6-OH dopamine within the neuron. This neurotoxin is activated by a second oxidation. Both of these reactions are thought to occur as a result of oxygen free radical production and attack on the dopamine, a naturally occurring neurotransmitter. These oxygen radical mediated oxidations are thought to occur at a relatively slow rate and to be responsible for the progressive loss of motor function in Parkinsonism and related conditions. Based upon the demonstration that chronic administration of PBN can decrease the progressive oxidation that occurs following a stroke, it is believed that PBN and other spin-trapping compounds will be effective in limiting the production of the neurotoxic dopamine oxidation products.

Concussion

The majority of the research literature indicates that concussion produces the bulk of its long term effects via interruption of brain and spinal cord microcirculation, producing localized ischemia. This interruption in blood flow can be the result of the initial trauma and shearing of capillaries or the consequence of the brain edema and compression of the blood vessels. In any event, spin trapping compounds are of therapeutic value as they have been demonstrated to be in models of stroke.

Berry Aneurysm and other types of aneurysm

This vascular problem results in bleeding on the brain and presents as a serious and chronic headache or other neurologic symptom. The condition is ultimately treated by surgical repair of the vessel that has developed a weak wall. However, this condition often results in hemorrhage and neural damage due to the bleeding. In addition, the presence of blood on the outside of the vessel sensitizes the vessels to spasm and increases the risk of a stroke, as is also true in concussion and other traumatic conditions. In addition to the radicals generated by spasm and stroke, the iron or other metal catalyzed generation of oxygen free radicals, similar to what has been proposed for ischemia and concussion, also represents a second source of free radicals.

Ventricular Hemorrhage and Associated Vasospasm

The same biochemical and physiological conditions as described for Berry Aneurysm and their management by spin trapping compounds will apply for these conditions.

Migraine and other Vascular Headaches

Migraines are thought to arise in part from large vessel vasodilation and compression of the microcirculation of the cortex. This is another form of ischemia/reperfusion injury. While spin-trapping compounds will not prevent the initial occurrence of these vascular headaches, they limit the extent or frequency by trapping the free radicals that are generated during the ischemia phase.

Spinal Cord Trauma

Spinal cord trauma involves the interruption of the normal vascular supply due to shearing forces at the time of the initial trauma and as a result of the subsequent edema of the tissue. In addition, the hemorrhage that often accompanies such trauma will also generate vasospasm and directly generated oxygen free radicals. Spin trapping compounds limit this process and terminate the intracellular cascade of lipid and protein oxidation.

Neuroanesthesia Adjunct

Several procedures involve resection of brain tissue which will result in hemorrhage in the immediate area. Other surgical procedures may be associated with increased risk of cerebral blood flow interruption, either as a natural consequence of the procedure, e.g., cardiac surgery or heart transplantation, or due to the unexpected interruption of flow, e.g., hemorrhage, clot following angioplasty, cardiac arrest during surgery. In all of these conditions, spin-trapping compounds will limit free radical mediated damage, and will limit the development of antigenic reactions or other changes in the vascular endothelium that will increase the risk of the development of a reaclusive injury. Reduction in free radical mediated damage limits antigen/antibody mediated tissue damage.

Peripheral Nervous System Diseases

Diabetics are well known for their tendencies to develop peripheral neuropathies and progressively lose sensation in limbs. In addition, diabetics have a higher risk to develop atherosclerosis, which may affect microvascular function. One of the most frequently seen biochemical consequences of diabetes is excessive glycation of proteins. It is believed that following glycation, there is a burst of protein oxidation that is mediated by oxygen free radicals. It is thought that this process of excessive glycation is critical in the development of damage to neurons and axons in the diabetic. Since spin trapping compounds are quite effective in limiting intracellular free radical mediated damage, such compounds can be used in the chronic management of diabetic neuropathies and other long term adverse consequences of diabetes.

Traumatic Nerve Damage

Crushing injury to peripheral nerves, as in the hands, arms, and legs, involves interruption of blood flow (ischemia) and edema. Effective and prompt repair is dependent on the re-establishment of an effective oxygen and nutrient supply. Often recovering tissue tends to outgrow its blood supply and is restricted in recovery by the ischemia that occurs as the tissue outgrows the vascular supply. Spin-trapping compounds can be used to provide greater tolerance of partial hypoxia as vascular supply grows to reach the healing tissue. In addition, the same ischemia/hypoxia protection that occurs in the non-vascular tissue may also enhance the growth of the endothelia as the revascularization process occurs.

Peripheral Organ Diseases

Atherosclerosis (both diabetic and spontaneous

Diabetic atherosclerosis involves the abnormal and excessive glycation of protein in the vascular wall. As discussed above for diabetic neuropathy, this involves oxygen radical production and consequent further damage to cytosolic proteins. Spin-trapping compounds will prevent this abnormal processing of cellular protein and other cellular constituents. In vitro studies have been conducted that demonstrate that PBN inhibits or reduces oxidation of low density lipoprotein in plasma. Plasma samples were tested for oxidation of lipid measured using thiobarbituric acid reactive substance ($T_{BAR}$, nM) and % inhibition of oxidation calculated. Phosphate buffered saline (PBS) was added to controls, 0.1 mM PBN was added to test samples, and the controls and sealed samples incubated at 4° C. for seven weeks.

The results are shown in Table 1.

TABLE 1

Testing of antioxidation activity of PBN

| sample | control + PBS | Test (nM/ml) | % inhibition* |
| --- | --- | --- | --- |
| NP132 plasma | 0.55 | 0.45 | 18.2 |
| NP134 plasma | 0.18 | 0.14 | 22.2 |
| NP135 plasma | 0.32 | 0.25 | 21.9 |

TABLE 1-continued

Testing of antioxidation activity of PBN

| sample | control + PBS | Test (nM/ml) | % inhibition* |
| --- | --- | --- | --- |
| NP133 LDL | 0.54 | 0.28 | 48.1 |
| NP135 LDL | 0.33 | 0.11 | 66.7 |

*The actual percent inhibition in the presence of PBN is greater than the measured value due to interference in the assay by the PBN.

Chronic Obstructive Pulmonary Disease (COPD)

COPD has been demonstrated to involve the attack of interstitial alveolar macrophages on pulmonary tissue. Animal models of this clinical condition have demonstrated that increases or decreases in superoxide dismutase activity in the lung can result in decreases or increases in pulmonary pathology, respectively. An alternative approach is to provide to the pulmonary tissue, either via the pulmonary vascular supply or via the airway, radical spin-trapping compounds which will limit the peroxidation of pulmonary tissue and the consequent loss of alveolar tissue.

Pancreatitis

Pancreatitis is believed to be the result of ischemic or chemically derived peroxidation of pancreatic parenchyma. Alcoholic pancreatitis is probably due to the direct effects of the ethanol radical and the indirect vascular effects of acetaldehyde mediated direct damage to proteins and indirect damage via catecholamine release and mitochondrial metabolism. There is currently no treatment for acute pancreatitis. If the condition does not abate, it is generally regarded as fatal in the severe form. Spin-trapping agents can be used to mediate the acute reaction, allowing the patient time to recover.

Angioplasty

In the process of re-expanding or laser removal of atheroma, there are periods of ischemia and reperfusion of the vessel or energy mediated production of free radicals. Recent studies have demonstrated that during this period, superoxide and nitric oxide are produced. These products have been demonstrated to further damage the endothelium and may also remove or damage the natural relaxant systems that locally control the vascular tone. If uncontrolled, such changes are likely to result in an increased risk of re-occlusion of the same vessel. Spin-trapping compounds can prevent the generation of the oxy-radical cascade and thereby reduce the likelihood of reocclusion following angioplasty. In the diabetic, there is also an increased risk of cutaneous alteration associated with vascular dysfunction and poor perfusion of the dermis.

Multi-organ failure following trauma

A characteristic problem following extreme trauma is the development in the patient of a negative nitrogen balance, poor protein synthetic capacity, pulmonary dysfunction, and abnormal cytokine production. Tumor necrosis factor (TNF) is excessively elevated during this process. TNF is associated with the cellular generation of oxygen free radicals in tissue and may be one of the primary causes of this condition. The activation of macrophages and lymphocytes also plays a critical role in the condition. Free radical production by the white cells is part of the process of multiple organ damage. Spin-trapping compounds can prevent the propagation phase of this condition and limit the extent of cachexia and organ damage following severe trauma.

Diabetic Retinopathy

Diabetes is a disease of abnormal glycation and partial ischemia. Both conditions promote free radical production.

The relatively common condition of diabetic retinopathy is thought to involve a microvascular and protein dysfunction of the retina. Spin-trapping compounds can limit the glycation mediated production of free radicals and the damage caused by microvascular interruptions.

Burn Treatment and Healing

Healing from serious burns is limited by the inability of the repairing vascular system to supply the rapidly growing cutaneum. Periods of ischemia in the dermis will occur as the growing skin cannot be adequately supplied. This hypoxia or ischemia results in the production of oxygen free radicals and either limits the rate of recovery and/or promotes the generation of scar tissue. Systemic and topical spin-trapping compounds can be used to improve the rate of healing and decrease scar formation.

Ischemic Bowel Disease

Strangulation of the bowel is a condition that is frequently fatal in both humans and animals such as dogs, horses and cattle. Even after resection and anastomosis of the intestine, the prognosis is not good. The generation of ischemia derived oxygen radicals and damage to the intestine is considered to be a primary cause. There is no effective treatment to date.

Studies have demonstrated that ischemia induced intestinal edema can be prevented or reduced by a number of different spin-trapping compounds.

Endotoxin is a primary factor in the pathophysiology of equine gastrointestinal disorders and gram negative bacterial infections. The pathophysiological is similar to that characterizing colitis, salmonellosis, and neonatal septicemia. It is hypothesized that endotoxin produces its toxic effects by triggering "oxidative bursts" from sensitized macrophages. These bursts of $O_2$ radicals are intended to kill invading bacteria associated with the presence of endotoxin. However, they have the adverse effect of damaging the tissues in which they are produced and this tissue damage is presumably the molecular basis of the pathological changes associated with endotoxin shock. Spin-trapping compounds have the ability to trap radicals and alleviate many of the toxic effects associated with radical formation. Additionally, recent experiments demonstrate that spin trap molecules protect rats against endotoxin administration.

Wound and Ulcer Healing

Tissue healing often involves periods of hypoxia or ischemia as the recovering tissue outgrows the vascular supply. Spin-trapping compounds can decrease the damage associated with this period of ischemia.

Infections as consequence of the development of decubitus ulcers is the number one cause of death in the elderly. The general clinical impression is that elderly patients are much more likely to develop these ulcers, compared to young adults. Pressure sores develop as a result of the interruption of blood flow to the skin. This process is identical to the process of ischemia/reperfusion oxidation of brain and other tissues. In the geriatric and/or diabetic patient, pressure sores may develop due to enhanced oxidation of the cells of the skin. Based upon the observations that spin-trapping compounds can prevent ischemia/reperfusion injury to both brain and intestine, it is expected that spin trapping compounds will reduce or prevent pressure sores. In addition, these compounds can be used systemically or topically in enhancing recovery.

Reduction in Side-effects of Cancer Chemotherapy

A number of cancer chemotherapeutic agents produce their cytotoxic effects via the production of oxygen free radicals within the cell. The limiting side effects of these compounds are also the result of oxygen free radical production in normal cells. Bleomycin produces pulmonary and cutaneous toxicities as a result of hydroxyl free radical production. Adriamycin produces cardiac and gastrointestinal side-effects. The spin-trapping compound PBN has been demonstrated to trap the free radicals produced by adriamycin in heart, brain and other organs of research animals, using the spin-trapping compound PBN. These spin-trapping compounds can be used to limit side effects in tissues, such as the brain and heart, that are especially vulnerable to develop free radicals, without compromising the therapeutic value of the chemotherapeutic agent.

Skin, Muscle Flap and Organ Survival Following Transplantation

Autologous (self) transplantation of skeletal muscles from one area to another should not involve any immunologic incompatibilities. However, estimates from one surgeon suggest that the success rate is more in the area of 50% success. Acceptance of skin flap grafts has an equally low success rate. It is postulated that much of the problem arises as a result of ischemia and reperfusion during the surgical procedures for removal and implantation. Following ischemia these tissues undergo calcium loading and eventually necrosis, as in strokes. Spin-trapping compounds can be used to limit the damage undergone by these tissues, as well as other organs, during surgery associated with transplantation.

Organs for transplantation are obtained from donors. The success of the procedure is determined in part by the age (oxidation) related reduction in organ viability, the amount of time the organ is in preservation solution, and the status of the recipient. Previous research has demonstrated that spin-trapping compounds can improve the enzymatic status of the aged brain, restoring enzymatic levels to near those of the young adult as early as seven days following initiation of daily treatment with a spin-trapping agent such as PBN.

Organ preservation solutions are designed to prepare the organ to be transplanted for the period of extracorporeal storage. The most recently developed solution contains glutathione as an antioxidant. Spin-trapping compounds differ from glutathione in that they can function both as antioxidants, trapping oxygen free radicals, as well as trapping compounds for both intracellular and extracellular carbon-centered free radicals.

It is believed organ survival would therefore be enhanced by administering spin-trapping compounds to the recipient, as well as adding the compounds to the organ preservation solution.

Ionizing Radiation Prophylaxis.

Ionizing radiation as a therapeutic modality and as an environmental toxicant causes its effects by producing hydroxyl free radicals intracellularly and extracellularly. Ultraviolet radiation acts similarly. The cascade that follows is functionally identical to the process of cellular damage caused by ischemia/reperfusion injury to tissue. Spin-trapping compounds can be used to selectively treat those tissues that are not involved by the cancer, thereby increasing the effectiveness of the therapy and decreasing the side effects of radiation therapies. In the case of environmental exposures, spin-trapping compounds should be effective both as a prophylaxis, applied topically or systemically, as well as a post-exposure therapeutic.

Treatment of Renal Hypertension Disorders, Resulting from Low Renal Artery Flow and High Renin Renal hypertension develops as a result of reduced blood flow to the kidney. The juxtaglomerular apparatus (JGA) recognizes this hypoperfusion and releases renin, which results in an angiotensin II mediated increase in blood pressure (hypertension). Hypoperfusion (hypoxia) is a condition that is known to result in significant oxygen free radical production, making it probable that oxygen free radicals are likely to be involved in the release of renin by the JGA, and therefore manageable at least in part through administration of spin-trapping compounds.

Exertional Injury to Skeletal Muscle

Sore muscles as a result of exercise are thought to be a consequence of free radical mediated peroxidation of skeletal muscle proteins and lipids. Since chronic treatment with spin-trapping compounds decreases cellular oxidations and protects enzymes from oxidative inactivation, daily treatment can be used to improve the process of exercise conditioning (especially in the horse). Moreover, aged skeletal muscle is likely to contain constituents, as do most other cells in the body. Since work has demonstrated that chronic administration of the spin-trapping compound PBN can return cells to the status of a young adult, spin-trapping can be used to improve the functional status and exercise condition of skeletal muscle in aged individuals.

Epistaxis (Pulmonary Bleeding in Horses) and Laminitis

Epistaxis (ES) and laminitis are both thought to involve ischemia/reperfusion injury to the alveolar basement membrane and the lamina propria of the hoof, respectively. Since both of these conditions involve the process of reperfusion generation of free radicals, spin-trapping compounds can be used in the prevention, management of treatment of these conditions.

Pharmaceutical Compositions

The spin trapping compounds are administered topically, locally, or systemically, depending on the application. When administered systemically, the compound is preferably administered orally or intravenously, in an appropriate pharmaceutical carrier such as saline or phosphate buffered saline (PBS) or in tablet form. For topical application, the compound is preferably administered in an ointment or cream base, or by means of a transdermal patch. The compound can also be administered by controlled delivery devices, such as biodegradable polymers, or by inhalation, insufflation or nasal spray. Suitable carriers are known to those skilled in the pharmaceutical area.

Effective dosages of Spin Trapping Compounds

A typical dose of the spin trapping agent for all of the above-mentioned conditions is in the range from about 0.1 to 100 mg/kg, preferably 0.5 to 50 mg/kg, of body weight per day. The effective dosage range of the pharmaceutically acceptable derivatives can be calculated based on the weight of the parent spin trapping compound to be delivered. If the derivative exhibits activity. in itself, the effective dosage can be estimated as above using the weight of the derivative, or by other means known to those skilled in the art.

The compound is conveniently administered in any suitable unit dosage form, including but not limited to one containing 5 to 2000 mg, preferably 50 to 1500 mg of active ingredient per unit dosage form. A oral dosage of 50–1000 mg is usually convenient.

Ideally the active ingredient should be administered to achieve peak plasma concentrations of the active compound of from about 0.5 to 100 mM, preferably about 1 to 30 mM.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Exemplary dosages of the parent phenyl t-butyl nitrone administered intravenously range from 0.1 to 10 mg/kg of body weight in animals. The effective dosage of PBN in humans for treating age and ischemic related disorders is expected to be between approximately 1 and 10 mg/70 kg body weight. Toxicity tests have demonstrated that PBN is completely innocuous, with such low toxicity that it was not possible to determine an $LD_{50}$. It is possible to extrapolate from comparative tests using other spin trapping compounds what the effective dosage for these compounds will be.

Since the trapping of endogenous free radicals is specific for only those cells that have been exposed to the conditions that result in the. production of free radicals, the traps have little or no effect on normal cells. The beneficial effects occur only in injured cells, and do not require the presence of specific receptors, specific enzymes, and/or specific cell types.

Methods of Administration of PBN

The spin trapping compound is preferably administered systemically, most preferably intravenously or orally, since these are the most rapid and efficient means for delivering the active compound to the site of free radical generation. The spin trapping compound may be administered at once, or may be divided into a number of smaller doses to be administered at varying intervals of time. Other methods of systemic administration can also be used, including inhalation or insufflation, subcutaneous, intravenous, and intraperitoneal administration. The spin trapping compound can also be administered topically, in an ointment, creme, or transdermal patch.

The spin trapping composition can be provided in the form of a pharmaceutically acceptable salt. As used herein, the term pharmaceutically acceptable salts or complexes refers to salts or complexes of that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with polyvalent metal cations such as zinc, calcium, bismuth, barium, magnesium, aluminum, copper, cobalt, nickel, cadmium, sodium, potassium, and the like, or with an organic cation formed from N,N-dibenzylethylenediamine, ammonium, or ethylenediamine; or combinations of (a) and (b); e.g., a zinc tannate salt or the like.

A preferred mode of administration of the active compound is in a form for oral delivery. Oral compositions will generally include an inert diluent or an edible carrier. Preferred pharmaceutical carriers for intravenous administration are saline or phosphate buffered saline at physiological pH. Since some compounds are pH sensitive, stability of the compound in the carrier should be determined and the pH of the carrier adjusted appropriately, or the compound administered in combination with food, a buffering agent, or in an enteric coating. For oral delivery, the spin trapping compound may be enclosed in capsules, compressed into tablets, microencapsulated, entrapped in liposomes, in solution or suspension, alone or in combination with a substrate immobilizing material such as starch or poorly absorbable salts such as immodium. Pharmaceutically compatible binding agents can be included as part of the composition. The tablets or capsules may contain, for example, any of the following ingredients, or compounds of a similar nature: a binder such as microcrystalline cellulose, gum tragacanth or gelatin; an excipient such as starch or lactose, a disintegrating agent such as alginic acid, Primogel©, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier. In addition, dosage unit forms can contain various other materials which modify the physical form of the dosage unit, for example, coatings of sugar, shellac, or other enteric agents.

Modifications and variations of the spin trapping compositions for the treatment of a variety of disorders associated with oxidation of proteins and/or lipids will be obvious to those skilled in the art from the foregoing detailed description. Such modifications and variations are intended to come within the scope of the appended claims.

We claim:

1. A method for the treatment of dysfunctions and disease conditions arising from oxidative damage comprising administering to a patient in need of such treatment an effective amount of a compound of the formula

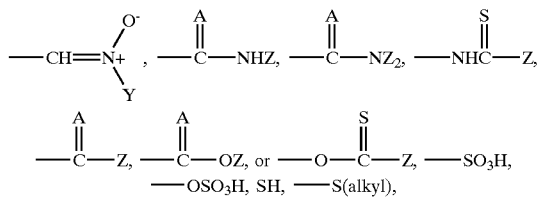

wherein:

X is imidazolyl, phenothiazinyl or

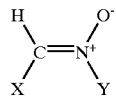

n=1–5;

$R^2$=independently (can vary within the molecule) halogen, alkyl, alkenyl, oxyalkenyl, $NH_2$, NHZ, $NZ_2$, NO,

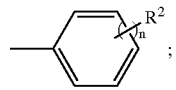

—S(alkenyl), and haloalkyl;

A=O or S; and

Z is a $C_1$ to $C_6$ straight or branched alkyl or cyclic group; and

Y is a tert-butyl group that can be hydroxylated or acetylated at one or more positions; phenyl or

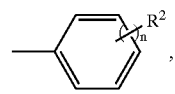

with the proviso that (a) both X and Y do not simultaneously represent

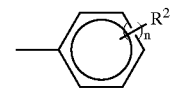

wherein n is 1 to 5 and wherein $R_2$ is halogen, alkyl, $NH_2$, —S(alkyl), haloalkyl, or

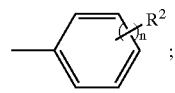

where Z is a $C_{1-6}$ straight or branched chain alkyl; and (b) where Y is phenyl, then X does not represent

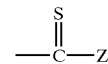

where n is 1 to 5 and wherein $R_2$ is halogen or alkyl.

2. The method of claim 1 wherein the disorder is of the central and peripheral nervous system and disorders of the peripheral organs.

3. The method of claim 2 wherein the disorder is a disorder of a peripheral organ.

4. The method of claim 3 wherein said peripheral organ is the skin.

5. The method of claim 1 wherein the disorder is selected from the group consisting of stroke, Parkinsonism, concussion, aneurysm, ventricular hemorrhage and associated vasospasm, migraine and other vascular headaches, spinal cord trauma, diabetic retinopathy and neuroanesthesia adjunct.

6. The method of claim 1 wherein the disorder is selected from the group consisting of diabetic peripheral neuropathy and traumatic nerve damage.

7. The method of claim 1 wherein the disorder is selected from the group consisting of atherosclerosis, chronic obstructive pulmonary disease, pancreatitis, pulmonary fibrosis due to chemotherapeutic agents, angioplasty, burns, ischemic bowel disease, ulcers and bed sores, lupus, ulcerative colitis, organ transplantation, renal hypertension, overexertion of skeletal muscle and epistaxis.

8. The method of claim 1 wherein the disorder is the result of exposure to cytotoxic compounds and radiation selected from the group consisting of X-ray, ultraviolet, gamma or beta radiation.

9. The method of claim 8 wherein the radiation is ultraviolet radiation.

10. The method of claim 1 wherein said compound is administered topically.

11. The method of claim 10 wherein said compound is administered in conjunction with an ointment or cream base suitable for topical administration.

12. The method of claim 1 wherein said compound is administered in conjunction with a pharmaceutically acceptable carrier.

13. The method of claim 1 wherein said compound is administered in a pharmaceutically acceptable carrier selected from the group consisting of carriers for intravenous administration, oral administration, administration via the respiratory tract, subcutaneous administration, intramuscular administration, rectal administration and topical administration.

14. The method of claim 1, wherein Y is a tert-butyl group that can be hydroxylated or acetylated.

15. The method of claim 1, wherein Y is phenyl.

16. The method of claim 1, wherein Y is

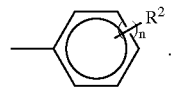

17. The method of claim 1, wherein X is imidazolyl.

18. The method of claim 1, wherein X is phenothiazinyl.

19. The method of claim 1 wherein X is

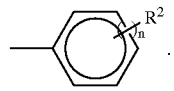

20. The method of claim 1 wherein Z is alkyl.

* * * * *